US010893682B2

(12) United States Patent
Brocheret et al.

(10) Patent No.: US 10,893,682 B2
(45) Date of Patent: Jan. 19, 2021

(54) PROCESS FOR DIRECT INOCULATION FROM CONCENTRATED FERMENTS AND ASSOCIATED DEVICE

(71) Applicant: Chr. Hansen A/S, Hoersholm (DK)

(72) Inventors: Sylvain Brocheret, Paris (FR); Marc Faiveley, Villenave d'ornon (FR); Anne-Claire Bauquis, Epernay (FR)

(73) Assignee: CHR. HANSEN A/S, Hoersholm (DK)

( * ) Notice: Subject to any disclaimer, the term of this patent is extended or adjusted under 35 U.S.C. 154(b) by 680 days.

(21) Appl. No.: 15/315,924

(22) PCT Filed: Jun. 2, 2015

(86) PCT No.: PCT/EP2015/062224
§ 371 (c)(1),
(2) Date: Dec. 2, 2016

(87) PCT Pub. No.: WO2015/185535
PCT Pub. Date: Dec. 10, 2015

(65) Prior Publication Data
US 2017/0094986 A1     Apr. 6, 2017

(30) Foreign Application Priority Data

Jun. 3, 2014 (FR) ..................................... 14 55037

(51) Int. Cl.
*C12M 1/00* (2006.01)
*C12M 3/00* (2006.01)
(Continued)

(52) U.S. Cl.
CPC ................ *A23C 9/12* (2013.01); *A23C 9/123* (2013.01); *A23C 9/1238* (2013.01); *C12M 23/32* (2013.01);
(Continued)

(58) Field of Classification Search
None
See application file for complete search history.

(56) References Cited

U.S. PATENT DOCUMENTS

| 4,856,563 A * | 8/1989 | Yamaguchi | ............... B65B 3/28 141/1 |
| 2002/0054936 A1 * | 5/2002 | Hoier | ..................... A23C 9/122 426/61 |

(Continued)

FOREIGN PATENT DOCUMENTS

| CN | 104837352 A | 8/2014 |
| EP | 0 611 820 A1 | 8/1994 |

(Continued)

OTHER PUBLICATIONS

PCT International Search Report issued in Application No. PCT/EP2015/062224 dated Aug. 25, 2015.
(Continued)

*Primary Examiner* — Nathan A Bowers
(74) *Attorney, Agent, or Firm* — Foley & Lardner LLP

(57) ABSTRACT

Process for continuous inoculation of a food product, in particular a dairy product, with ferments, comprising the following steps: —solid concentrated ferments are transformed into liquid concentrated ferments, —the transformed concentrated ferments are continuously injected into a flow of liquid to be inoculated, characterized in that the liquid concentrated ferments are transformed—by thawing frozen concentrated ferments in a temperature controlled chamber or—by rehydrating freeze-dried concentrated ferments.

7 Claims, 5 Drawing Sheets

Figure 1:
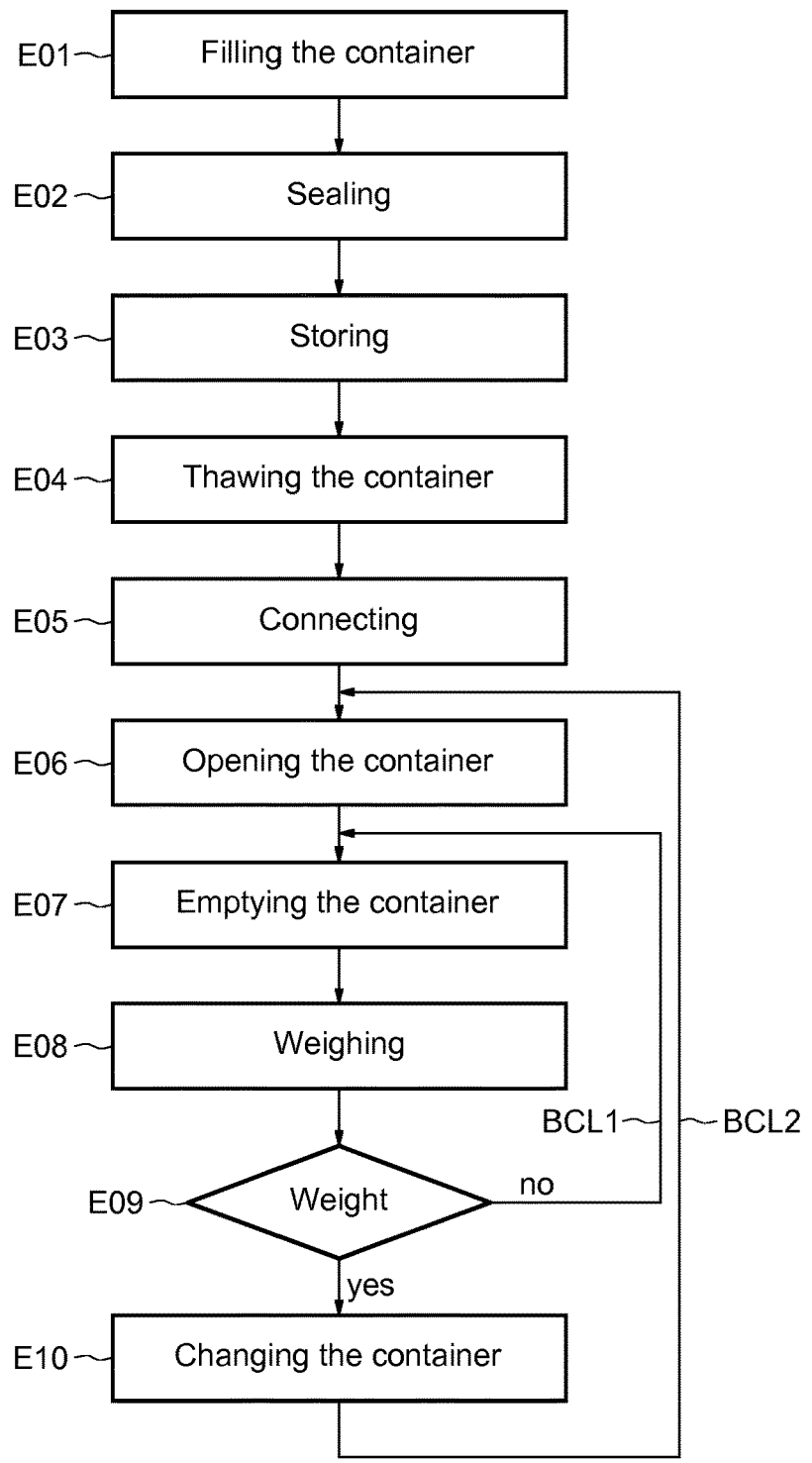

(51) Int. Cl.
*A23C 9/12* (2006.01)
*A23C 9/123* (2006.01)
*C12N 1/20* (2006.01)
*C12M 1/26* (2006.01)
*C12M 1/06* (2006.01)
*C12M 1/34* (2006.01)

(52) U.S. Cl.
CPC ............ *C12M 27/02* (2013.01); *C12M 29/14* (2013.01); *C12M 33/00* (2013.01); *C12M 41/14* (2013.01); *C12M 41/40* (2013.01); *C12M 41/44* (2013.01); *C12N 1/20* (2013.01); *A23V 2002/00* (2013.01); *A23Y 2240/75* (2013.01)

(56) References Cited

U.S. PATENT DOCUMENTS

| | | | |
|---|---|---|---|
| 2006/0040340 A1* | 2/2006 | Greene | C12M 33/04 435/34 |
| 2006/0110512 A1* | 5/2006 | Blomme | B67D 1/1227 426/523 |
| 2008/0145481 A1 | 6/2008 | Posseme et al. | |
| 2015/0366231 A1 | 12/2015 | Poignand et al. | |
| 2018/0179479 A1 | 6/2018 | Kristine et al. | |

FOREIGN PATENT DOCUMENTS

| FR | 2 710 073 A1 | 3/1995 |
|---|---|---|
| FR | 2 873 384 A1 | 1/2006 |
| WO | WO 99/09838 | 3/1999 |
| WO | WO 99/09838 A1 | 3/1999 |
| WO | WO 01/70935 A2 | 9/2001 |
| WO | WO 2014/086671 A1 | 6/2014 |

OTHER PUBLICATIONS

PCT International Preliminary Report on Patentability issued in Application No. PCT/EP2015/062224 dated Dec. 6, 2016.

* cited by examiner

PROCESS FOR DIRECT INOCULATION FROM CONCENTRATED FERMENTS AND ASSOCIATED DEVICE

The present invention relates to an equipment and a process for continuous inoculation from concentrated ferments requiring neither incubation or preculture which have a potential health risk, nor interruption of the inoculation process during production.

Inoculation in the food-processing industry and in the dairy industry in particular is of essential importance for producing a product. Indeed, the industrial and qualitative performance levels of the final products depend on the nature and the efficiency of the ferments used and on their method of addition.

The obtaining of precultures, also known as starter cultures, i.e. prior to activation of the culture in order to reduce the lag phase, for the inoculation of milk is known from documents WO 200170935 and EP688864. Patent application WO 99/09838 describes a method for preparing a fresh product in which the starter culture can be in frozen form.

The fermentation of liquid medium to be inoculated with frozen concentrated ferments means that the manufacturer using them has to work in batchwise mode for the inoculation and fermentation phases. Indeed, since the form and type of packaging is generally as bags or tins, the microorganisms must necessarily be added directly to the fermentation tank.

Other systems using concentrated ferments require the presence of a supplemental container for intermediate thawing of the ferments in case of frozen ferments or for dilution in case of dried ferments, which increases the risk of contaminations.

These reactivation and/or dilution systems have the drawback of making it necessary to handle the concentrated ferments upstream of the inoculation phase, thereby risking contaminations.

The applicant has discovered surprisingly that the introduction of frozen concentrated ferments can be carried out by direct inoculation.

Alternatively, the freeze-dried concentrated ferments can be introduced by direct inoculation.

This allows continuous inoculation without having to interrupt the fermentation process for the production of the final product. It thus becomes possible to substantially increase fermented product production rates.

The subject of the invention is thus a process for continuous inoculation of a food product, in particular a dairy product, with concentrated ferments.

According to one general characteristic, the process comprises the following steps:

either frozen concentrated ferments are thawed in a temperature controlled chamber, such as a refrigerator, operating on a container containing frozen concentrated ferments, or the freeze-dried ferments are rehydrated.

the concentrated ferments obtained are continuously injected, from the container, into a flow of liquid to be inoculated.

The subject of the invention is also an equipment for continuous inoculation of ferments into a liquid to be inoculated, wherein the ferments originate from either frozen or freeze-dried concentrated ferments, said equipment comprising either a temperature controlled transforming chamber for thawing a container comprising frozen concentrated ferments, or a transforming chamber in which the freeze-dried ferments are rehydrated in the container, an inoculation chamber provided with support means for installing at least two containers of ready-to-use ferments and with at least one weighing device capable of continuously determining the remaining volume in the container being emptied, the equipment further comprising an injection circuit connecting the containers to a circuit for continuous feeding of the liquid to be inoculated, the injection circuit comprising a valve allowing switch from one container to another container and means for regulating the flow rate of the ferments in liquid form.

In one embodiment, the container containing the frozen concentrated ferments is stored at a temperature of −20 to −70° C. prior to the thawing thereof.

In an other embodiment, the container containing the freeze-dried concentrated ferments is stored at a temperature of −20 to ambient temperature prior to rehydration.

The container may be rigid, deformable, soft. Preferentially, the container is soft.

Advantageously, once placed in the inoculation chamber, the container containing the ready-to-use concentrated ferments is continuously weighed in order to determine, during emptying, the remaining volume of liquid ferments in the container weighed.

The injection of the ferments is carried out via means of connection to a circuit for continuous feeding of liquid to be inoculated. These connection means may be pipes of an injection circuit, which can be cleaned and sterilized after each passage of the liquid to be inoculated in the line, or more or less flexible tubing provided with means of temporary connection, for example via clip-fastening or snap-fastening.

Microbial contamination of surfaces constitutes a danger to health through the possible contamination of foods during transformation thereof. This is, for example, the case when bacterial spores occur in biofilms, i.e. multicellular communities of microorganisms adhering to one another and to a surface. Indeed, bacterial spores exhibit remarkable resistance characteristics and contaminate the surfaces of the equipment and of connecting piping. For industrial manufacturers, the removal of biofilms in most cases requires the use of excessive hygiene procedures in order to ensure good preservation of the transformed foods, and to avoid food contaminations.

Thus, alternatively, the means of connection to a circuit for continuous feeding of liquid to be inoculated are disposable in order to ensure perfect sterility and easy use. These means of connection may also be changed according to the ferments used.

Preferably, the container after thawing or after rehydrating is placed in an inoculation chamber at a pressure above atmospheric pressure.

Thus, in one embodiment of the invention, the inoculation chamber containing the concentrated ferments is pressurized by means of a neutral sterile gas in order to maintain as far as possible in said chamber a constant pressure which thus facilitates the accuracy of the flow of the concentrated ferments. Furthermore, an overpressure in the container limits the possibilities of contamination by outside air. An overpressure typically of 100 $g/cm^2$ allows a more even metering.

In one embodiment of the invention, several containers are placed in parallel arrangement in the inoculation chamber so that, when one of them is in the process of being emptied, at least one other container containing ready-to-use concentrated ferments is on standby.

Preferably, by means of this process, a metered amount of ready-to-use concentrated ferments is continuously introduced into a flow of liquid to be inoculated. This inoculated liquid will then be put in a fermentor, a tank for producing fermented products or a fermentation device, directly in the container intended to be marketed. In the case of a dairy product, for example, the fermentation unit may be a pot of dairy product.

This continuous inoculation has the effect of improving the regularity of the quality of the final products. The invention thus allows direct use, from their container, of the previously frozen or freeze-dried concentrated ferments directly in the line of liquid to be inoculated without involving a risky intermediate phase. Any intermediate handling phase indeed inevitably leads to risks of accidental contamination which are detrimental to the whole of the subsequent process for producing the fermented product. Furthermore, directly inoculating into the line of liquid just before renneting makes it possible to limit any proliferation of phages and the creation of biofilms on the maturation zone.

Preferably, means for regulating the flow rate of the ferments in liquid form are placed upstream of the circuit for continuous feeding of the liquid to be inoculated. These means may be a pump.

The thawing time for the frozen concentrated ferments in the container is variable depending on the amounts of products present in the container.

The thawing time for the frozen concentrated ferments in a temperature controlled chamber is from 5 to 30 hours, and preferably around 12 hours.

In order to ensure a homogeneous melting of the concentrated ferments without creating any large thermal shock which would be detrimental to the correct course of the subsequent steps of the production process, the temperature in the transforming chamber is regulated.

Preferably, the temperature of the atmosphere in the temperature controlled chamber is from 0 to 15° C. and preferably 4° C.

Preferably, the frozen concentrated ferments are stirred during the thawing in order to homogenize them and to avoid incompletely melted aggregates.

The rehydrating time for the freeze-dried concentrated ferments in the container is variable depending on the amounts of products present in the container. It is generally from 30 minutes to 2 hours, and preferably around 1 hour.

Preferably, the freeze-dried concentrated ferments are stirred during the rehydrating in order to homogenize them and to avoid incompletely rehydrated aggregates.

For this purpose, in one embodiment of the equipment, the temperature controlled transforming chamber may comprise means for stirring the container.

Once placed in the inoculation chamber, the ready-to-use liquid ferments are maintained at a relatively low temperature which may be from 2 to 12° C., or any other temperature compatible with maintaining the functionalities of the ferments. This makes it possible to limit as much as possible the resumption of the bacterial metabolism and to guarantee a quality of inoculation which is constant over time.

In one embodiment of the equipment, the inoculation chamber may comprise refrigeration means and means for maintaining the pressure above atmospheric pressure.

The inoculation chamber of the equipment may advantageously comprise means of homogenization of at least one container during emptying.

Thus, homogenization of the mixture of concentrated ferments during emptying makes it possible to ensure the homogeneity of the mixture of bacterial cultures constituting the ferments.

Preferably, the homogenization step comprises blending.

The frozen or freeze-dried concentrated ferments can be packaged and stored in packaging with a more or less large capacity ranging from 200 g to several kilos. The transfer must be carried out under strict hygiene conditions in order to avoid any contamination detrimental to the whole of the subsequent fermentation process.

The concentrated ferments used are composed of bacteria which are used for producing cheeses such as, for example, soft cheeses, cooked pressed cheeses, uncooked pressed cheeses, spun-curd cheeses, and fermented milks such as, for example, stirred or set, flavoured or natural yoghurts, drinking yoghurts, crème fraîche and fromages frais and also for producing other fermented products such as, for example, wine.

The bacteria used may be mesophilic microorganisms, the optimum growth temperature of which is from 25 to 35° C. Among the mesophilic microorganisms typically used, mention may in particular be made of, for example, *Lactococcus lactis* subsp. *lactis*, *Lactococcus lactis* subsp. *cremoris*, *Leuconostoc cremoris*, *Lactoccus lactis* biovar. *diacetylactis*, *Lactobacillus casei*, *Streptococcus durans*, *Streptococcus faecalis*.

Use may also be made of thermophilic microorganisms, i.e. organisms of which the growth temperature may be from 35 to 45° C. Mention may in particular be made of, for example, *Streptococcus thermophilus*, *Lactobacillus lactis*, *Lactobacillus helveticus*, *Lactobacillus delbrueckii* subsp. *bulgaricus* and *Lactobacillus acidophilus* or any other appropriate microorganism.

Likewise, strictly anaerobic microorganisms of the bifidobacteria type, including *Bifidus bifidum* and *Bifidobacterium longum* (*animalis*) can be used.

Use may also be made of propionic bacteria such as *Lactobacillus helveticus*, *Propionibacterium freudenreichii*, *Propionibacterium freudenreichii* subsp *shermanii*, etc.

The bacteria used may be wine bacteria, for example *Oernococcus oeni* (*Leuconostoc oenos*), *Lactobacillus plantarum* or *Pedicoccus* sp.

Use may also be made of yeasts of the family Saccharomycetaceae or moulds such as *Penicillium* or *Geotrichum*.

The level of ready-to-use concentrated ferment or concentrated bacterial culture inoculation varies according to the technologies and the products under consideration. Generally, this proportion is from 0.005% to 0.025% based on the total weight of the medium to be inoculated.

Generally, upon being produced, the ferments are frozen using liquid nitrogen, then stored at a temperature from −20 to −70° C.

Depending on their freezing temperature, the frozen ferments can be stored for some time before use: up to 1 month in case of storing at −20° C., up to 6 months in case of storing at −40° C., and up to 12 months in case of storing at −45° C.

Alternatively, the freeze-dried ferments are dried by sublimation of the frozen water from a frozen culture by reducing pressure in the surrounding allowing the water to evaporate directly to gas without going by liquid phase. For the purpose of the invention, the expressions freeze-drying, lyophilisation and cryodesiccation have the same signification.

Freeze-dried fements are generally stored at −20° C. In this case, the shelf life can be up to 24 month. It can also be stored at +5° C. but in this case its shelf life is about 6 weeks.

Figure 2:
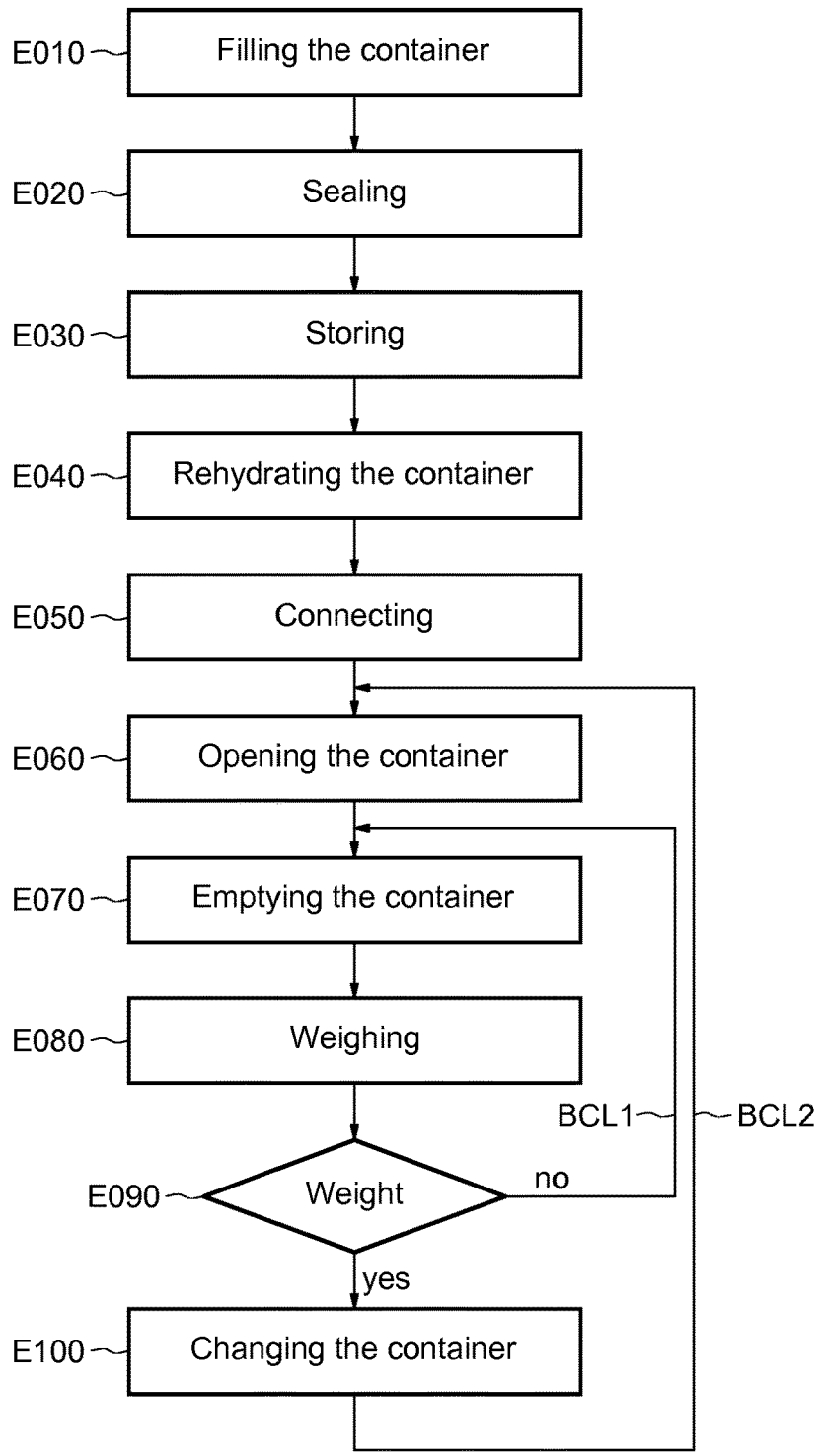
Figure 3:
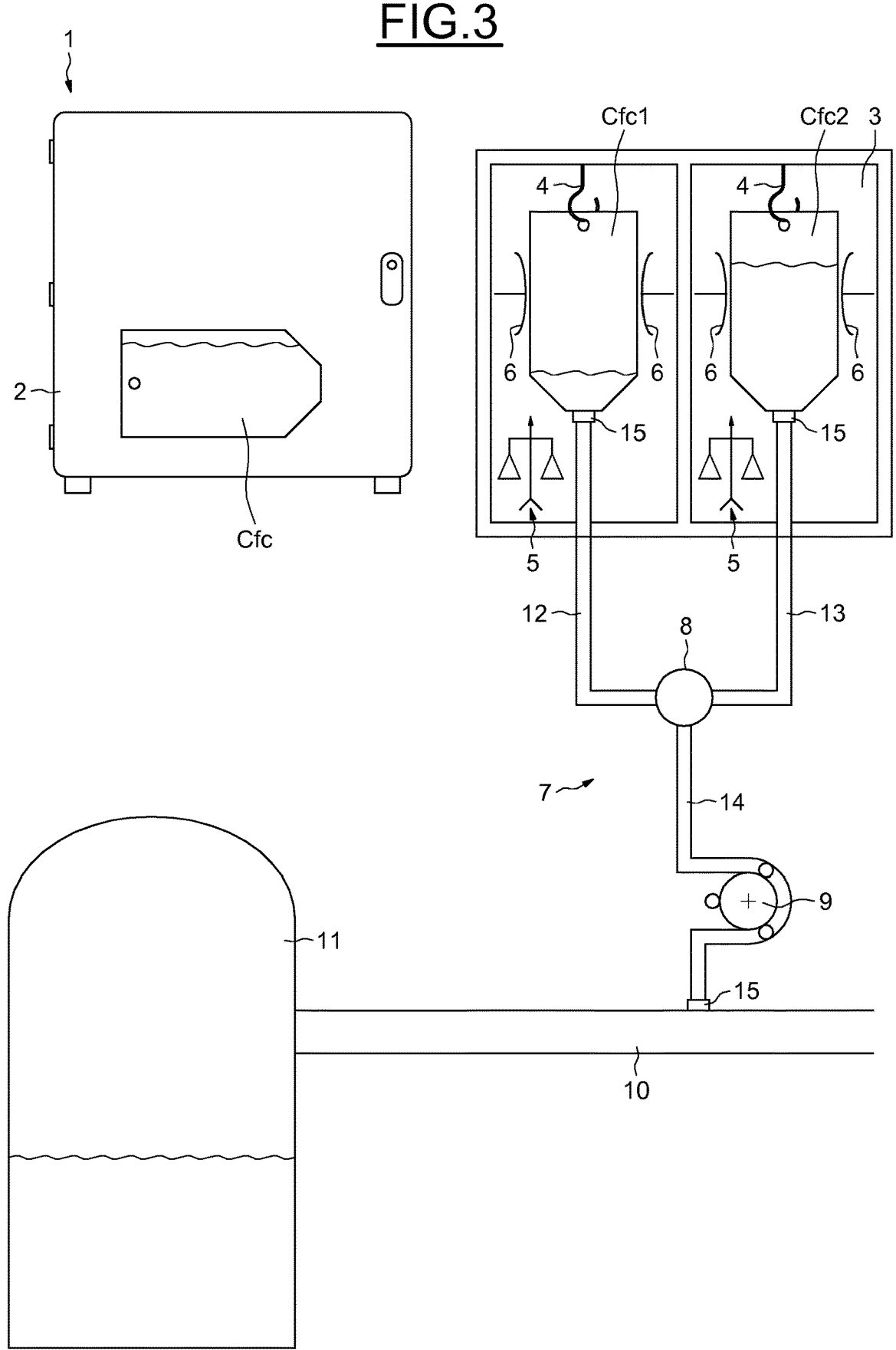
Figure 4:
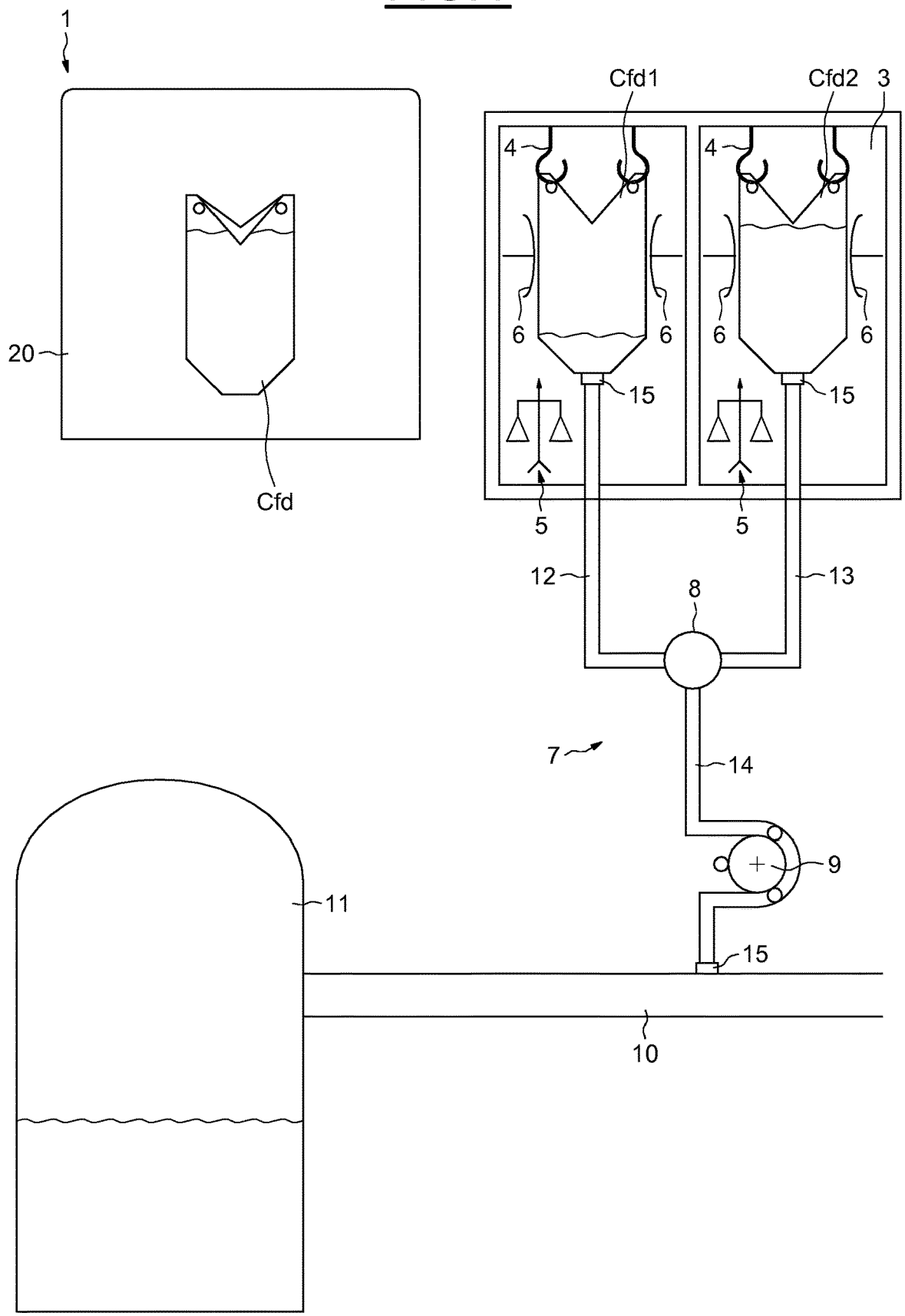
Figure 5:
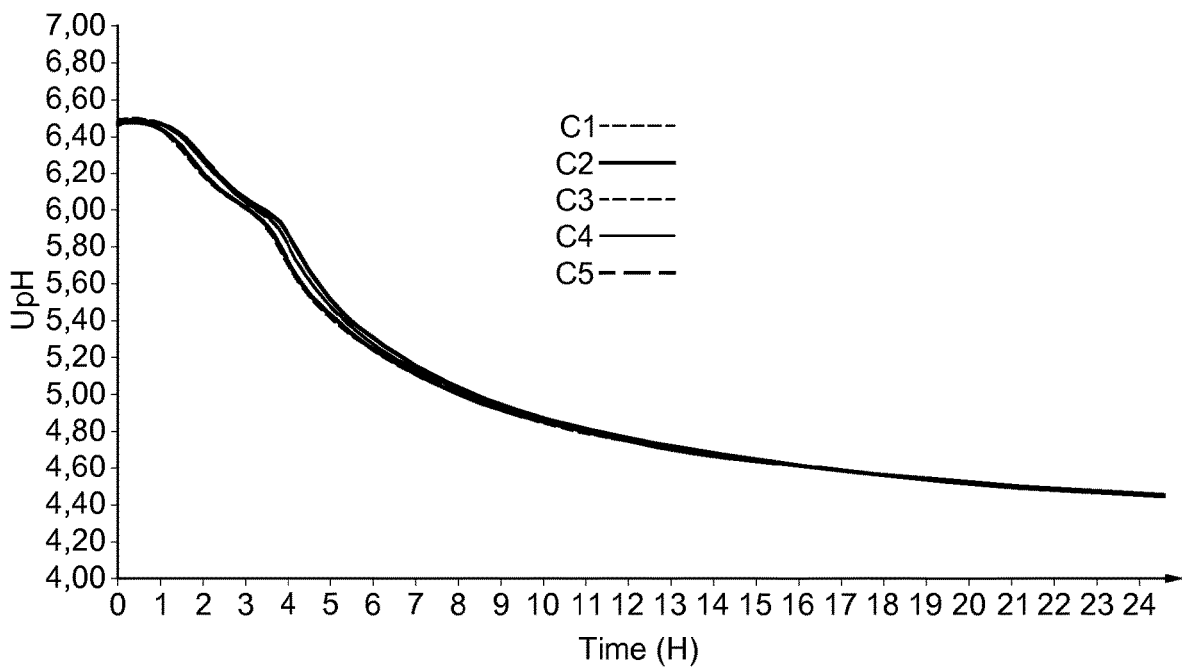
Figure 6:
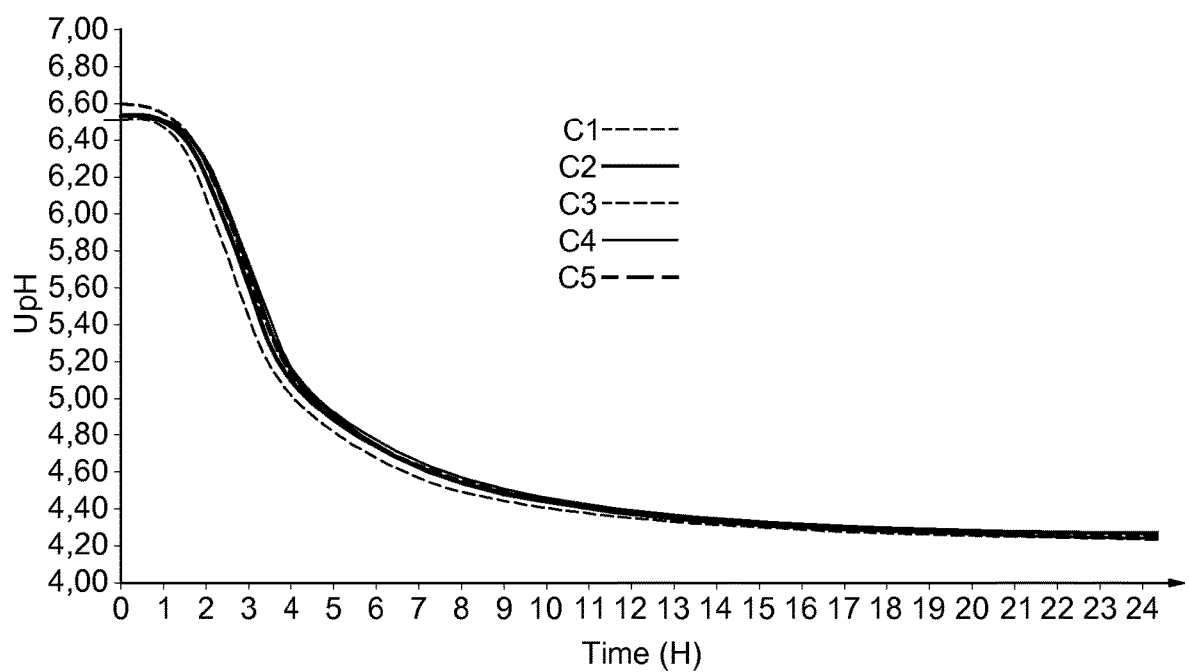

Other purposes, characteristics and advantages will appear upon reading the following description of an embodiment and of different modes of implementation of the invention, given only as nonlimiting examples, and given with reference to the attached drawings in which:

FIG. 1 illustrates schematically a flowchart of the various steps of a process according to one mode of implementation of the invention, FIG. 2 illustrates schematically a flowchart of the various steps of a process according to a second mode of implementation of the invention, FIG. 3 illustrates schematically a first embodiment according to the invention, FIG. 4 illustrates schematically a second embodiment according to the invention, FIG. 5 represents monitoring curves for the acidification of the culture medium at 40° C. of the SSC100 culture after thawing, as a function of the thawing time 0 h, 24 h, 48 h 72 h or 96 h in the refrigerator, FIG. 6 represents monitoring curves for the acidification of the culture medium at 37° C. of the STI06 culture after thawing, as a function of the thawing time 0 h, 24 h, 48 h 72 h or 96 h in the refrigerator, Represented schematically in FIG. 1 is a flowchart of the various steps of an inoculation process according to one embodiment of the invention.

Prior to the inoculation, concentrated ferments are frozen. Then they can be blended and packed in containers.

For this, in a first step E01, a container is sterilely filled with concentrated frozen ferments. The containers may be packagings of more or less large capacity ranging from 200 g to several kilograms that are capable of maintaining concentrated ferments composed of bacteria that are used for producing cheeses, fermented milks and other fermented products.

Then, in a step E02, the orifice of the container is sealed, still while maintaining sterility, so as to obtain a hermetically sealed container filled with concentrated ferments.

In a subsequent step E03, these frozen ferments are stored at a temperature from −20 to −70° C. for a relatively long time of a few days to several months.

It is possible to repeat steps E01 to E03 with different containers so as to obtain a plurality of containers comprising the same frozen concentrated ferments.

For the inoculation, in step E04, frozen ferments are thawed in situ in one of the containers previously kept frozen. By "in situ", it is meant that the ferments stored in the container are transformed in the same container into liquid concentrated ferments without transfer. This thawing step is carried out via refrigeration means acting on the container and more particularly on the frozen ferments contained in the container. In the embodiment presented, the frozen concentrated ferments are stirred during the thawing, in order to distribute the heat evenly and to avoid incompletely melted aggregates.

In a subsequent step E05, the container which has undergone thawing is connected to a disposable injection circuit.

In a subsequent step E06, the container connected to the injection circuit is installed in an inoculation chamber and the container is opened.

The thawed container is then emptied in a step E07. During the emptying, the inoculation chamber is pressurized with a neutral sterile gas in order to maintain a constant pressure therein as much as possible and thus to facilitate the accuracy of the flow of the concentrated ferments. The thawed liquid ferments are also maintained at a temperature from 2 to 12° C., so as to limit as much as possible the resumption of the bacterial metabolism and to guarantee an inoculation quality which is constant over time.

While being emptied, the container is regularly weighed, in a step E08, so as to determine the amount of ferments remaining in the container.

Next, in a step E09, the weight measured in the preceding step is compared to a threshold value corresponding to the weight of the empty or almost empty container. In addition, depending on the weight of the container, and therefore depending on the amount of ferments remaining in said container, the container-emptying operation is continued by resuming it in step E07 via a loop BCL1, or the virtually empty container is exchanged with a full thawed container in a step E10. The thawing of the full container may have been initiated during the emptying of the previous container, or before the beginning of the emptying of said previous container, for example after the beginning of the thawing of said previous container using another thawing chamber.

These steps of emptying a container, weighing, and optionally changing container according to the volume of remaining ferments are carried out via a loop BCL2.

The parallel arranging of several containers in an inoculation chamber and step E10 of exchanging a container to be emptied make it possible to obtain a continuous inoculation process wherein a metered amount of thawed concentrated ferments is continuously introduced into a flow of liquid to be inoculated, wherein the inoculated liquid can then be introduced in a fermentor, a tank for producing fermented products or a device for fermentation, directly in the container intended to be marketed.

This continuous inoculation results in improving the regularity of the quality of the final products.

Represented schematically in FIG. 2 is a flowchart of the various steps of an inoculation process according to a second embodiment of the invention.

Prior to the inoculation, concentrated ferments are freeze-dried. Then they can be blended and packed in containers.

For this, in a first step E010, a container is sterilely filled with concentrated freeze-dried ferments. The containers may be packagings of more or less large capacity ranging from 200 g to several kilograms that are capable of maintaining concentrated ferments composed of bacteria that are used for producing cheeses, fermented milks and other fermented products.

Then, in a step E020, the orifice of the container is sealed, still while maintaining sterility, so as to obtain a hermetically sealed container filled with concentrated freeze-dried ferments.

In a subsequent E030, these ferments are stored at a temperature of −20° C. for a relatively long time of a few days to 24 months.

It is possible to repeat steps E010 to E030 with different containers so as to obtain a plurality of containers comprising the same freeze-dried concentrated ferments.

For the inoculation, in step E040, freeze-dried ferments are rehydrated in situ in the container previously stocked. By "in situ", it is meant that the ferments stored in the container are transformed in the same container into liquid concentrated ferments. In this case, the rehydrating step is carried out in the container itself without transfer of the ferments from another container.

In a preferred embodiment, the container containing the ferments comprises a packaging forming a two-compartment container, the first compartment comprising the freeze-dried ferments separated by a breakable membrane from the second compartment comprising the sterile liquid in which the ferments are rehydrated once the breakable membrane between the two chambers is broken.

In the embodiment presented, the concentrated ferments are stirred during the rehydrating, in order to avoid incompletely dissolved aggregates.

In a subsequent step E050, the container which has undergone rehydrating is connected to a disposable injection circuit.

Steps E060 to E100 are the same as the steps of the inoculation process of FIG. 1.

Represented schematically in FIG. 3 is an inoculation equipment 1 according to a first embodiment of the invention. The equipment 1 comprises a thawing chamber 2 comprising a refrigerator capable of thawing a container of frozen concentrated ferments Cfc according to step E04 of the process illustrated in FIG. 1. The thawing chamber 2 comprises means for stirring the ferments during the thawing, which are not represented in the figure, for homogenization of the ferments.

The equipment 1 also comprises an inoculation chamber 3. The inoculation chamber illustrated in this figure comprises two support means 4 each capable of supporting a container of thawed concentrated ferments Cfc1 and Cfc2, for example a vertical attachment device or a device for gripping the container, comprising a set of plates for holding the container in place and/or a hook. It is possible to store certain types of concentrated ferments once thawed in the inoculation chamber 3 for several hours and up to 24 hours, but preferably between 4 and 8 hours without particular effect on the resumption of the bacterial metabolism or on the activity of the bacteria constituting the concentrated ferments.

The inoculation chamber 3 of the equipment 1 comprises, moreover, means 5 for weighing the container in order to deduce the volume of the remaining ferments during emptying (steps E07 to E09). The inoculation chamber 3 also comprises homogenization means 6 for homogenizing the ferments located in the container. By way of nonlimiting example, use may be made of a plurality of plates applying a different pressure per plate which varies with passing time. The homogenization can be carried out continuously or intermittently as required.

In addition, the inoculation chamber 3 may comprise air-conditioning means not represented in FIG. 2. Thus, the inoculation chamber 3 can be refrigerated at a temperature of from 2 to 12° C. throughout the duration of the inoculation.

The inoculation chamber 3 may comprise a plurality of means for supporting the container of thawed concentrated ferments Cfc, the Cfc containers being connected via an injection circuit 7 to a circuit for continuous feeding 10 of the liquid to be inoculated. In the embodiment illustrated in FIG. 2, the injection circuit 7 comprises a valve 8 connected to a first container Cfc1 via a first circuit portion 12, to a second container Cfc2 via a second circuit portion 13 and to the feeding circuit 10 via a third circuit portion 14. The valve 8 thus makes it possible to change container Cfc1 or Cfc2 without interrupting the injection process.

The injection circuit 7 also comprises a pump 9 installed on the third circuit portion 14, consequently downstream of the valve 8. The pump 9 serves to regulate the flow rate of afferent liquid concentrated ferments of the container Cfc1 or Cfc2 in place in the inoculation chamber 3. The regulating pumps used, such as pump 9, can be proportioned according to the flow rate of the main circuit of the medium inoculated; typically in the dairy industry, the pump flow rates range from 0.1 l/hour to 4 l/hour, for equipment of 2 to 10 000 l/hour, up to 0.75 l/hour to 12 l/hour for equipment of 15 000 to 30 000 l/hour.

The injection circuit 7 may also comprise connecting means 15 at the level of the container(s) Cfc1 and Cfc2 in the inoculation chamber 3, and at the level of the junction between the circuit portion 14 and the feeding circuit 10.

These connecting means 15 make it possible to sterilize and clean the injection circuit 7 more easily. In another embodiment, these connecting means make it possible to change the portions 12, 13 and 14 of the injection circuit 7 in order to replace them with others which are sterile, during, for example, the changing in the composition of the ferments being used to inoculate the pipe 10 for feeding of the liquid to be inoculated.

The inoculation chamber 3 may also comprise means, not represented in the figure, for checking the pressure inside the inoculation chamber 3.

The equipment 1 also comprises a fermentation unit 11 connected to the circuit 10 for feeding the liquid to be inoculated. The inoculation of said liquid is carried out by means of a tapping on the pipe of the feeding circuit 10, making it possible to connect the third circuit portion 14 of the injection circuit 7.

The fermentation unit 11 is in this case reproduced in the form of a fermentor. Of course, it is also possible to envisage that the fermentation unit 11 is a tank for producing fermented products or a device for fermentation directly in the container intended to be marketed, for example a pot of dairy product.

The quantification of the thawed ferments is an essential part of the fermentation unit inoculation process.

Represented schematically in FIG. 4 is an inoculation equipment 1 according to a second embodiment of the invention.

The equipment 1 comprises a transforming chamber 2 comprising the container containing the concentrated ferments Cfd rehydrated according to step E040 of the process illustrated in FIG. 2. The transforming chamber 2 comprises means for stirring the ferments during the rehydrating, which are not represented in the figure, for homogenization of the ferments.

The equipment 1 also comprises an inoculation chamber 3. The inoculation chamber illustrated in this figure comprises four support means 4, capable of supporting the containers of rehydrated concentrated ferments Cfd1 and Cfd2, for example a vertical attachment device or a device for gripping the container, comprising a set of plates for holding the container in place and/or a hook. It is possible to store certain types of concentrated ferments once rehydrated in the inoculation chamber 3 for several hours and up to 24 hours, but preferably between 4 and 8 hours without particular effect on the resumption of the bacterial metabolism or on the activity of the bacteria constituting the concentrated ferments.

Same parts as in FIG. 3 are assigned the same reference numbers.

Whatever the embodiment of the invention, the inoculation equipment makes it possible to obtain a continuous and accurate on line flow of a small amount of concentrated ferments from concentrated ferments for inoculating a fermentation unit. The invention thus allows to directly use from their container the concentrated ferments, directly in the line of liquid to be inoculated without a risky intermediate phase being involved. Any intermediate handling phase in fact inevitably leads to risks of accidental contamination which are detrimental to the whole of the subsequent process for producing the fermented product. Furthermore, directly inoculating into the line of liquid just before renneting makes it possible to limit any possible phage proliferation.

EXAMPLE 1

Monitoring the Acidification of the Culture Medium Following Thawing Using a Refrigerator Device The ferments SSC-100 (*Streptococcus thermophilus* with a slow acidification) and STI06 (*Streptococcus thermophilus* with a rapid acidification) are packaged in sterile pouches of 5 litres, i.e. 2.5 kg of ferments in a form of frozen granules stored at a temperature of either −40° C. or −20° C.

The pouches are placed in a refrigerator.

The ferments previously stored at −40° C. were subjected to refrigeration for 12 hours to achieve complete melting.

The pouches are placed on a stirrer throughout the thawing in order to ensure homogeneous melting of the concentrated ferments.

The tests for acidification of the culture medium were carried out on milk reconstituted at 9.5% solids content from skimmed milk powder, heated at 99° C. for 30 min. The inoculation dose is, 0.01% for SSC-100 with a maturation temperature of 40° C. and 0.01% for STI06 with a maturation temperature of 37° C.

The results of the monitoring of the acidifying activity of each of the strains tested are given below as curves of variation in pH of the inoculated medium as a function of time, the test strains having been previously thawed in a refrigerator device (FIGS. 5 and 6).

In particular, FIG. 5 represents monitoring curves for the acidification of the culture medium of the SCC-100 culture, FIG. 6 represents monitoring curves for the acidification of the culture medium of the STI06 culture, after thawing in a refrigerator as a function of the time in the refrigerator.

In each of the figures, the first curve referenced C1 corresponds to the control for culture of the ferments without previous thawing, and curves C2 to C5 represent the curves obtained after thawing during thawing time of respectively of 24, 48, 72 or 96 hours.

The acidification monitorings for the various strains tested allow one to deduce that there is no significant effect of the thawing time in a refrigerator of the ferments on the acidifying activity performance levels.

Thus, it was demonstrated that it is possible to thaw various types of frozen concentrated bacterial cultures for several hours at a temperature of 2 to 12° C. without particular effect on the resumption of the bacterial metabolism and on the activity, in particular acidifying activity, of the ferments under consideration.

The invention claimed is:

1. Equipment for continuous inoculation of ferments into a liquid to be inoculated, the ferments being thawed, liquid ferments originating from frozen concentrated ferments, the equipment comprising:

a temperature controlled chamber configured to thaw a container containing frozen concentrated ferments, to transform the frozen concentrated ferments into thawed, liquid ferments inside the container, an inoculation chamber comprising a support configured to support at least two said containers containing thawed, liquid ferments, and at least one weighing device configured to continuously determine a remaining volume of thawed, liquid ferments in at least one of the at least two said containers, wherein the inoculation chamber comprises at least one homogenizer configured to homogenize at least one of the at least two said containers, and an injection circuit configured to connect said containers to a circuit configured to continuously feed the thawed, liquid ferments into a liquid to be inoculated, wherein the injection circuit comprises a valve configured to switch between said containers and a regulator configured to regulate the flow rate of the thawed, liquid ferments.

2. Equipment according to claim 1, wherein the temperature controlled chamber comprises a refrigerator.

3. Equipment according to claim 1, wherein the temperature controlled chamber comprises a stirrer.

4. Equipment according to claim 1, wherein the inoculation chamber is configured to be pressurized above atmospheric pressure.

5. Equipment for continuous inoculation of ferments into a liquid to be inoculated, the ferments being rehydrated, liquid ferments originating from freeze-dried concentrated ferments, the equipment comprising:

a first chamber configured to receive a container containing freeze-dried concentrated ferments configured to be rehydrated inside the container to be transformed into rehydrated, liquid ferments inside the container, an inoculation chamber comprising a support configured to support at least two said containers containing rehydrated, liquid ferments, and at least one weighing device configured to continuously determine a remaining volume of rehydrated, liquid ferments in at least one of the at least two said containers, wherein the inoculation chamber comprises a homogenizer configured to homogenize at least one of the at least two said containers, and an injection circuit configured to connect said containers to a circuit configured to continuously feed the rehydrated, liquid ferments into a liquid to be inoculated, wherein the injection circuit comprises a valve configured to switch between the at least two said containers and a regulator configured to regulate the flow rate of the rehydrated, liquid ferments.

6. Equipment according to claim 5, wherein the first chamber comprises a stirrer.

7. Equipment according to claim 5, wherein the inoculation chamber is configured to be pressurized above atmospheric pressure.

* * * * *